(12) United States Patent
Durán Vargas et al.

(10) Patent No.: US 12,303,648 B2
(45) Date of Patent: May 20, 2025

(54) DEVICE TO PREVENT APNEA EPISODES IN INFANTS

(71) Applicant: PONTIFICIA UNIVERSIDAD CATÓLICA DE CHILE, Santiago (CL)

(72) Inventors: Alejandro Alfonso Durán Vargas, Providencia (CL); María Jesús Alvarez Irarrázaval, Lo Barnechea (CL); Paulina Alejandra Toso Milos, Lo Barnecheao (CL)

(73) Assignee: PONTIFICIA UNIVERSIDAD CATÓLICA DE CHILE, Santiago (CL)

( * ) Notice: Subject to any disclaimer, the term of this patent is extended or adjusted under 35 U.S.C. 154(b) by 983 days.

(21) Appl. No.: 17/311,295

(22) PCT Filed: Oct. 25, 2019

(86) PCT No.: PCT/CL2019/050105
§ 371 (c)(1),
(2) Date: Jun. 4, 2021

(87) PCT Pub. No.: WO2020/113350
PCT Pub. Date: Jun. 11, 2020

(65) Prior Publication Data
US 2022/0047841 A1  Feb. 17, 2022

(30) Foreign Application Priority Data
Dec. 5, 2018 (CL) .................................. 3478-2018

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2021/0088* (2013.01);
(Continued)

(58) Field of Classification Search
CPC .......... A61M 21/02; A61M 2021/0022; A61M 2021/0088; A61M 2205/0216;
(Continued)

(56) References Cited

U.S. PATENT DOCUMENTS

| 3,419,923 A | 1/1969 | Cowan |
|---|---|---|
| 4,606,328 A | 8/1986 | Thoman |

(Continued)

FOREIGN PATENT DOCUMENTS

| CN | 106310483 A | 1/2017 |
|---|---|---|
| DE | 10 2012 103 862 A1 | 11/2013 |

(Continued)

OTHER PUBLICATIONS

International Search Report (ISR) in related International Application No. PCT/CL2019/050105, mailed Feb. 13, 2020 (three pages).

*Primary Examiner* — Sunita Reddy
(74) *Attorney, Agent, or Firm* — Kilpatrick Townsend & Stockton LLP

(57) ABSTRACT

Device (1) for preventing apnea episodes in infants, which simulates a breathing pattern suitable for synchronizing the infant's breathing and which is provided as a tactile direct stimulus, arranged in contact with the infant's back while sleeping; it comprises a breathing pattern generator means (2) that emits air pulses that reach the infant through transmitter means comprising a flexible conduit (3) that transports the air to an inflatable/deflatable chamber (4).

18 Claims, 11 Drawing Sheets

(52) U.S. Cl.
CPC . *A61M 2205/0216* (2013.01); *A61M 2205/07* (2013.01); *A61M 2205/18* (2013.01); *A61M 2205/3331* (2013.01); *A61M 2205/42* (2013.01); *A61M 2205/581* (2013.01); *A61M 2205/583* (2013.01); *A61M 2209/088* (2013.01); *A61M 2240/00* (2013.01)

(58) Field of Classification Search
CPC .......... A61M 2205/07; A61M 2205/18; A61M 2205/3331; A61M 2205/42; A61M 2205/581; A61M 2205/583; A61M 2209/088; A61M 2240/00; A61H 9/0092; A61H 9/0078; A61H 2201/0184; A61H 2201/1207; A61H 2201/1619; A61H 2201/165; A61H 2201/5007; A61H 2201/5071; A61H 2203/0456; A61B 5/4818; A61B 5/4836; A61B 2503/04
USPC ...................................................... 600/26–28
See application file for complete search history.

(56) References Cited

U.S. PATENT DOCUMENTS

| | | | |
|---|---|---|---|
| 4,694,839 A | 9/1987 | Timme | |
| 5,205,811 A * | 4/1993 | Fornarelli | A47G 9/1045 600/28 |
| 5,277,194 A | 1/1994 | Hosterman et al. | |
| 5,395,301 A | 3/1995 | Russek | |
| 6,011,477 A * | 1/2000 | Teodorescu | A61B 5/0507 340/575 |
| 8,866,621 B2 | 10/2014 | Wolfe et al. | |
| 9,931,053 B1 | 4/2018 | Sham | |
| 10,201,236 B1 * | 2/2019 | Cloud | A47G 9/1045 |
| 2007/0240723 A1 | 10/2007 | Hong et al. | |
| 2008/0168994 A1 * | 7/2008 | Hong | A61F 5/56 128/848 |
| 2008/0178384 A1 * | 7/2008 | Lord | A47D 15/008 5/93.1 |
| 2013/0165809 A1 | 6/2013 | Abir | |
| 2013/0190554 A1 * | 7/2013 | Vogt | A63B 23/185 600/27 |
| 2014/0142652 A1 * | 5/2014 | Francois | A61B 5/0806 607/42 |
| 2014/0148720 A1 * | 5/2014 | Younes | A61H 9/0092 601/151 |
| 2014/0180036 A1 | 6/2014 | Bukkapatnam et al. | |
| 2016/0000640 A1 * | 1/2016 | Lai | G16H 20/30 601/149 |
| 2016/0165961 A1 * | 6/2016 | Karp | A61M 21/02 2/69.5 |
| 2019/0046072 A1 * | 2/2019 | Sham | A61B 7/00 |

FOREIGN PATENT DOCUMENTS

| | | |
|---|---|---|
| GB | 2 359 994 A | 9/2001 |
| JP | 2000-107154 A | 4/2000 |
| WO | 2016/139598 A1 | 9/2016 |

* cited by examiner

DEVICE TO PREVENT APNEA EPISODES IN INFANTS

This application is a U.S. National Phase of International Application No. PCT/CL2019/050105, filed Oct. 25, 2019, which claims priority to Chilean Patent Application No. 3478-2018, filed Dec. 5, 2018, the disclosures of which are incorporated by reference herein.

The invention being the subject of the present Patent of Invention application relates to a device which prevents apnea episodes in infants, preferably newborns, by simulating a breathing pattern suitable for synchronizing the infant's breathing and which is arranged in contact with the infant's back while sleeping.

DESCRIPTION OF THE PRIOR ART

Sleep apnea is a condition consisting of pauses in breathing during sleeping hours, in which the person does not breathe in or out for about 15 to 20 seconds.

Episodes of apnea and respiratory pause are common events occurring in newborns and infants, where respiratory pauses may be normal at different ages; however, they should be considered abnormal if they are greater than 20 seconds in duration or if they produce associated hypoxemia or cyanosis and the frequency of apnea increases during active sleep (rapid eye movements).

A significant part of young infants susceptibility to apnea and respiratory pauses is related to the development of breathing control that occurs within the first months of life.

There are several types of apnea—central, obstructive and mixed—with the central apnea being the one of importance for this invention, and being the one in which the air blockage between the nose and the mouth is associated to a lack of respiratory movements in thorax and abdomen, it is due to the immaturity of the breathing control centers. It is more frequent during the first six months of life and usually appears with two pauses of less than 10 seconds.

Apnea is more frequent the more immature the newborn is; it is present in 50-60% of preterm infants, 40% of which being of central origin, 10% obstructive and 50% mixed. Almost all premature infants stop suffering from apnea pauses when reaching an age equivalent to 37 weeks of gestation. Apnea of prematurity is all the more frequent the lower the gestational age and in the most immature infants it frequently persists beyond 34 weeks and sometimes even beyond 40 weeks postconceptional age. Sometimes in apnea of prematurity the attacks occur repeatedly, simulating periodic breathing.

The respiratory health of the child is also a point of concern for newborns and infants, as sudden infant death syndrome (SIDS) is a syndrome characterized by the sudden and unexpected death of an infant. According to several studies, infants who die of SIDS have abnormalities in the brain stem (medulla oblongata), which helps control functions such as breathing, blood pressure, and arousal. 2.6.

The importance of parents, such as the mother's voice, heartbeat, breathing, and body temperature to a newborn baby's early development has been established, and intimate cuddling has been shown to stabilize heart rate and breathing, even preventing sudden infant death syndrome, especially in premature newborns that often experience difficulty coordinating their heart rhythms with breathing.

For example, reductions in parent-to-child temperature transfer, parent-to-child voice transfer, and parent-to-child heartbeat transfer have been shown to increase respiratory pauses and apnea in infants and decrease oxygen level.

Research has shown that deprivation of maternal biological rhythms may be a cause of irregular behavior and sleep patterns in premature infants.

There have been several studies of management and treatment with non-pharmacological measures, some of which being interventions that have been shown to be helpful in reducing the occurrence and frequency of apnea of prematurity (leaving aside intervention on secondary causes that provoke or promote it). Such interventions include: proper positioning of the infant during sleep to maintain a patent airway, with the aid of "nests" that position the body to avoid flexion of the head over the trunk or prone position.

There is another theory supporting the recommendation to place babies on their backs to sleep, based on the fact that babies sleep more soundly when placed on their stomachs and cannot be awakened when they have an incidence of sleep apnea, which is believed to be common in infants, so sleeping on the back has been recommended as a way to avoid episodes of apnea.

An important scope that has been studied as part of the management to reduce the incidence and frequency of apnea in children, is the effect produced by maintaining direct contact of the child with his mother or father, demonstrating that this contact produces a synchronization of the infant's heart and respiratory rhythm based on the stable biological parameters of the parents, especially by the transmission of the pattern of movement of the adult's chest to the child who is in direct contact. However, it has also been shown that what the infant needs is a breathing pattern that is appropriate for him/her and not the same pattern of an adult, since infants, especially newborns, have a much faster respiratory rhythm than adults.

Despite the above, there are drawbacks to carry out this attachment throughout the night or during the day when the infant sleeps, not only because there is a risk of crushing the baby if it is made to sleep in the same place as the adult, but also sometimes it is not possible because the child is in an incubator or in special supervised care. However, this trend has its detractors, based on studies that show the detrimental effect of stress states in the caregivers can be transferred to the baby, understanding that emotional episodes are expressed both in the cardiorespiratory rhythm, as well as in other physiological demonstrations of the person. This situation causes caregivers subjected to states of anguish, depression and other emotional disorders to affect the "quality" of the synchronization of the cardiorespiratory rhythm adequate for the infant.

This has led to research and development of devices that can mimic the sound of the heartbeat or the movement of the chest when breathing that can be transmitted to the infant without the need for direct contact with the adult.

In the field of solutions designed to address the problem of infants with apnea, there are two main groups, those that are based on constantly monitoring the infant's breathing and heartbeat, which in case of a departure from acceptable ranges emits an alarm to alert parents or caregivers and these intervene, usually by moving the child and changing its position.

Examples of that mentioned above are described in the U.S. Pat. No. 8,866,621 (B2) published on Oct. 21, 2014, where the system can detect the sleep position of a baby, provide a sensor signal to a filter that can filter the result and transmit a signal only when the result is indicative of a prone sleeping position (on the stomach) below, so that caregivers modify their position or in the application WO2016139598

(A1) published on Sep. 9, 2016 that shows an apparel with built-in sensors that constantly monitor the baby's signs and emit alert signals.

As can be seen, this type of solutions are warning and do not directly intervene in the inhibition of apnea episodes; therefore, devices have also been developed that in addition to this means of detection and alert, also have means to wake up or directly stimulate the infant and bring him/her out of apnea, those means being mostly vibration or electrical impulse transmission devices, as described in document CN106310483 (A) published on Nov. 1, 2017.

In these cases, while addressing the problem of bringing the infant out of the apnea episode, they are not preventive, but reactive means as a rapid response to bring the child out of the apnea episode.

Thus, it has become necessary to design solutions that generate a stimulus transmission environment in the infant, especially the sound of the mother's heartbeat, such as what is seen in the German patent DE102012103862 (A1) published on Jul. 11, 2013, which teaches a system for capturing the signs of the mother or caregiver, for simultaneous transmission towards the baby in incubator, which is achieved by a mattress with transducer units to generate sounds transmitted by the body and/or chest movements, described by the data stream, from a reference person.

The disadvantage of this system is that its conformation does not facilitate its use at home level and intervenes the environment where the child is placed, such as a "nest" where the child sleeps, where the position of the device with respect to the body is not assured, widening the possible range of error for the transmission of the stimulus in the precise area where the child is to feel it and additionally, as mentioned above, it cannot be assured that the cardiorespiratory rhythm of the caregiver is adequate for the infant if this person is under the effects of stress.

Similar disadvantages are seen in solutions that seek to transmit the simulated movement of the mother/father's breathing or of an adequate breathing pattern and that are based on providing an inflatable chamber, which, although they have the advantage of lower costs and simpler technology, these inflatable chambers are not placed directly on the infant to ensure the application of the stimulus in the specific area, but are applied in the environment, specifically in a mattress, as seen in documents GB2359994 (A) of Sep. 12, 2001 and U.S. Pat. No. 3,419,923 (A) of Jan. 7, 1969, or are applied in a toy to be placed attached to the child, as seen in U.S. Pat. No. 4,606,328 (A) of Aug. 19, 1986, however none of them ensures the position on the body.

In view of the foregoing, the present invention comes to overcome the problems of the prior art by providing a device for preventing or inhibiting episodes of apnea in infants, preferably newborns, which simulates a breathing pattern suitable for synchronizing the infant's breathing and which is arranged in contact with the infant's back while sleeping.

DESCRIPTION OF THE INVENTION

The main objective of the present invention is to provide a device capable of generating pressurized air pulses according to a repetitive pattern that simulates a normal or age-appropriate pattern and transmitting it to the infant as a tactile stimulus.

Another objective is to provide a device capable of securing its position on the infant's body, so that even if the infant moves or lies in a position other than dorsal decubitus, the device will still provide the stimulus.

Still another objective of the invention is to provide a device that permits positioning the provider of the direct stimulus on the infant, but that the components that generate the air pulses can be placed at a distance from him/her to avoid erroneous stimulations with operating sounds.

Thus, the present invention concerns a device for preventing apnea episodes in infants, preferably newborns, which simulates a breathing pattern suitable for synchronizing the infant's breathing and which is provided as a tactile direct stimulus arranged in contact with the infant's back while sleeping.

It comprises a breathing pattern generating means that emits pulses of air reaching the infant through stimulus transmitting means and ensures contact with the infant's body through an adaptive means that surrounds the infant's torso.

The simulated breathing pattern generator medium generates air pulses according to a repetitive regimen specific to each patient, based on a normal pattern, which in the case of newborns the normal respiratory rate ranges from 35 to 60 breaths per minute.

The simulated breathing pattern generating means preferably comprises an inflation means such as a pump and a deflation means such as a pneumatic control valve, which p supplies air and extracts it from time to time.

The breathing pattern generating means of the present invention may also comprise a mechanical or electromagnetic device, such as a motor, coupled to an inner diaphragm.

The breathing pattern generating means (2) is programmable by the user, for which purpose it comprises a central microcontroller (2b) that commands the operation of the components and provides different simulated breathing frequencies. The microcontroller may also be associated with a safety device (2c) with sensors (2c-1) to prevent over-inflation of the chamber and a visual or audible warning means (2c-2) in case of system failure to alert the caregiver or parent of the interruption in the supply of the stimulus, as shown in the schematic of FIG. 2B.

The breathing pattern generating means may also comprise a backup battery pack to ensure operation of the system in the event of interruption of the power supply that energizes the system.

This breathing pattern generator means also comprises a housing that houses its components and is formed by a body with at least one connection nozzle for air outlet/inlet, at least one interface panel for programming by the user and is made with noise insulating walls, formed by a top wall, a bottom wall and perimeter walls that form an inner cavity where the components are housed.

The housing comprises positioning means in the infant's environment, which allow it to be fixed to a support such as the bars of a crib or to be placed on a straight surface without slipping and falling.

These positioning means comprise a flexible band attached to the casing having adjustable fastening means, such as a sliding clasp or a contact clasp that allows the flexible bands to be passed through crib bars and attached to each other by the clasp, securing their position in the environment.

Alternatively, the housing may comprise bumpers of elastomeric material on its bottom wall giving it an anti-slip feature in case the housing rests directly on a surface external to the infant's crib.

The aforementioned simulated breathing pattern transmitting means comprises an inflatable/deflatable chamber that is attached to the infant and a flexible conduit that conveys air from the pump to the chamber.

The chamber is formed by two watertight sheets, an upper and a lower one joined at their perimeter edge, which retain an unattached area where a coupling mouthpiece is arranged.

In one embodiment of the invention, the upper sheet and the lower sheet are flexible made of elastomeric material, such as silicone, latex or rubber.

In an alternative embodiment of the invention the upper sheet is flexible and the lower sheet is rigid, so that as air enters or leaves the chamber, it is only one of the sheets that moves or deforms, while the opposite sheet remains rigid ensuring its adaptation and stabilization on the surface where the infant is lying.

The aforementioned flexible conduit that conveys air from the pump to the chamber is a hose that extends from the connection nozzle of the casing to the coupling nozzle of the inflatable chamber.

The body-fitting means conforming to this device comprises an inflatable chamber container with means for positioning on an article of apparel and means for arranging the flexible conduit.

The flexible chamber container is a pocket with a side opening for passage of the flexible conduit to the outside, wherein this pocket is positioned on the outside or inside of the back area of an article of clothing that is positioned surrounding or hugging the torso of the infant, so as to secure the position of the chamber against the child's back.

In a preferred embodiment, the apparel piece is a fabric that wraps around the infant's torso and has openings for passage of the arms, with a side opening for passage of the flexible conduit to the outside of said apparel in case the chamber container pocket is arranged on the inside of the apparel piece.

In another alternative embodiment, the garment is a waistband adjustable to the circumference of the child's torso, under the child's arms.

In a preferred embodiment, the pocket is formed of a single flexible cover and is integrated into the back area of the piece of garment, either on the inner side or the outer side of the piece of garment.

In another embodiment, the pocket is formed by two soft flexible covers, incompletely joined at their perimeter leaving an access opening for inserting the inflatable chamber and comprises removable adhesion means on one of its covers allowing it to be attached to a piece of garment, wherein said removable adhesion means of the pocket comprise a contact adhesive patch arranged on the outer or inner surface of one of the covers of the pocket allowing it to be attached to the piece of garment.

The device may be arranged in a unitary form for individual use, especially in home use or alternatively, it may be arranged as a set for hospital use, where the breathing pattern generation means has a larger capacity pump, such as to supply three or four devices at a time, which may be arranged in a larger housing in close proximity to the infant units, and provide each unit with the means of inflating a chamber for each unit, where each unit also has a piece of garment that receives the chamber which is attached to the pump by its own flexible conduit.

DESCRIPTION OF THE FIGURES

For the implementation of the foregoing and related objects, the invention may be carried out in the manner illustrated in the drawings attached; however, the drawings are only illustrative and they do not limit the scope of the invention. Variations are contemplated as part of the invention, limited only by the scope of the claims.

Thus, a detailed description of the invention will be carried out together with the figures which form an integral part of this presentation, wherein.

DETAILED DESCRIPTION OF THE INVENTION

The present invention relates to a device for preventing apnea episodes in infants, preferably newborns, which simulates a breathing pattern suitable for synchronizing the infant's breathing and which is provided as a direct tactile stimulus arranged in contact with the infant's back while sleeping.

Figure 1:
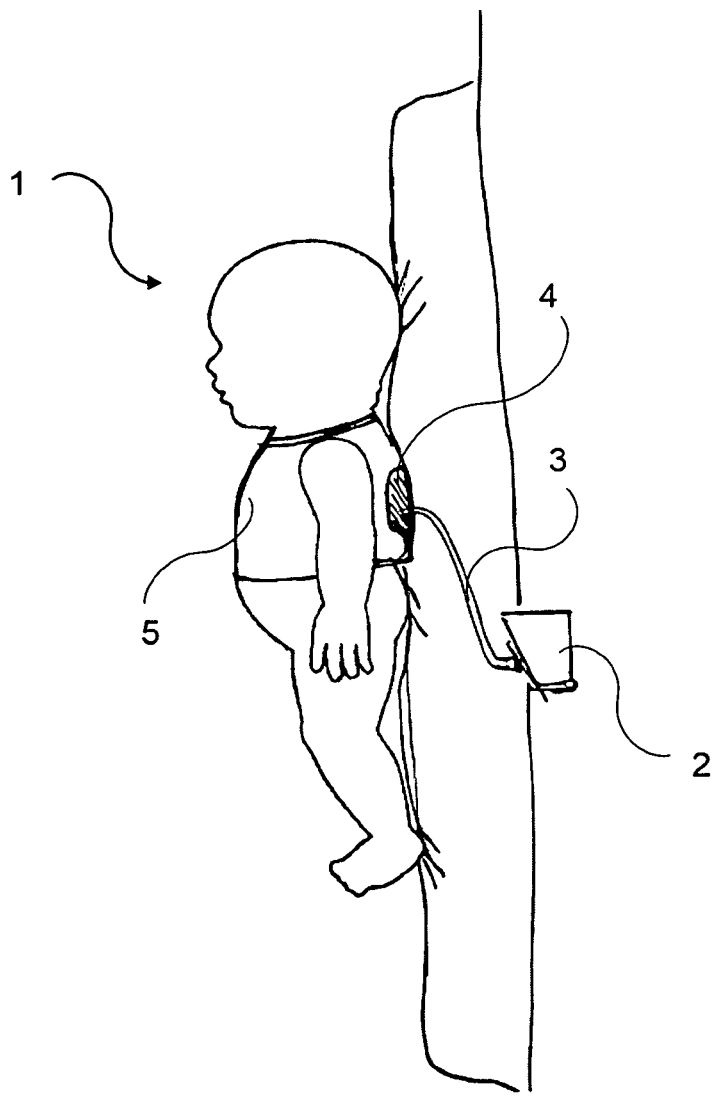
FIG. 1 shows a side view showing the device in use.

As illustrated in FIG. 1, the device (1) comprises a simulated breathing pattern generating means (2) that emits pulses of air reaching the infant through stimulus transmitting mean's (3) comprising an inflatable/deflatable chamber (4) and is secured in contact with its body by an adaptive means (5) surrounding its torso.

Figure 2A:
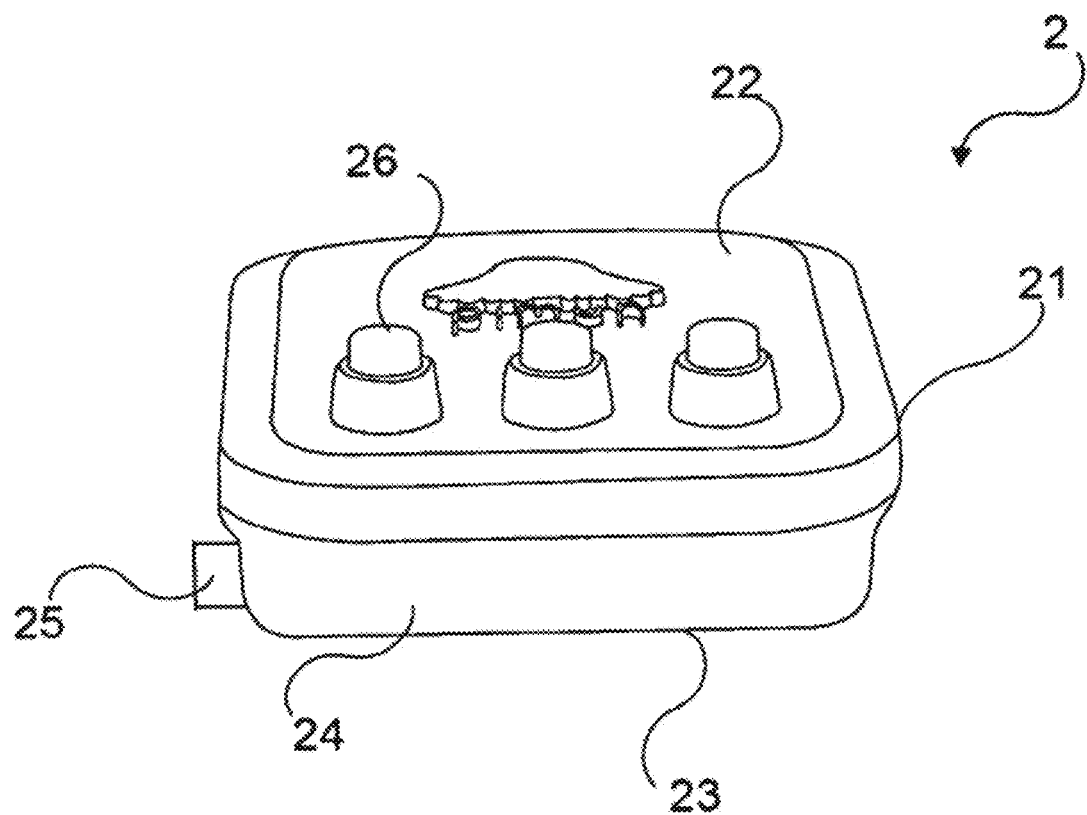
FIG. 2A shows an isometric view of the air pulse generating means.
Figure 2B:
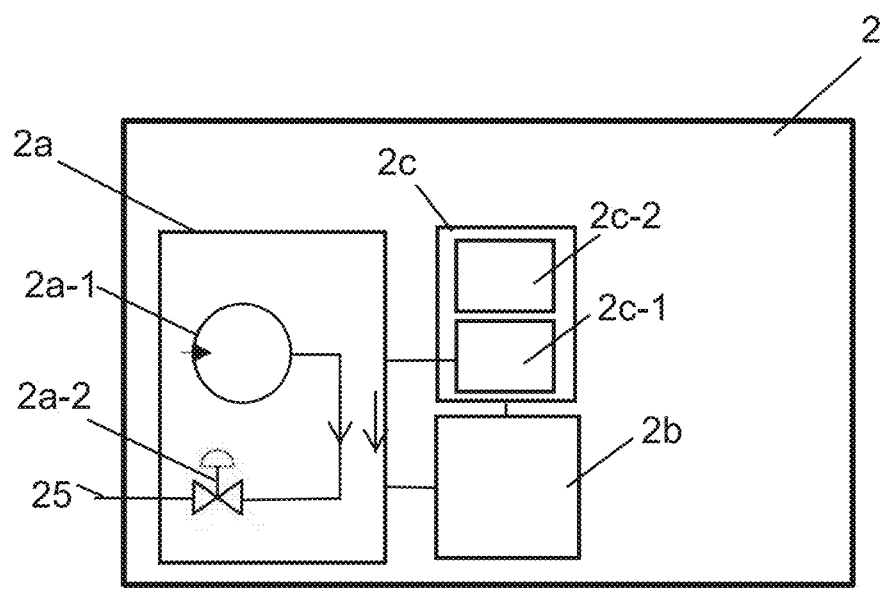
FIG. 2B shows a schematic of the breathing pattern generating means (2) and associated components.

The simulated breathing pattern generating means (2) comprises an inflation means (2a) such as an air pump (2a-1) and a deflation means such as a pneumatic control valve (2a-2), which supplies air and extracts it from time to time, as shown in the schematic of FIG. 2B.

This breathing pattern generator means (2) can be programmed by the user and generates air pulses according to a specific repetitive regime that simulates different breathing rates for each patient. To this effect, it comprises a central microcontroller (not illustrated) that commands the operation of the components and provides the different simulated breathing rates; it is associated with a safety means with pressure sensors that prevents over-inflation of the chamber, an audible or visual warning means in case of malfunction and a group of backup batteries that ensure the operation of the system in case of interruption of the power supply that energizes the device.

As best seen in FIG. 2A, the breathing pattern generating means also comprises a housing (21) which houses the components and is formed by a rigid body having a top wall (22), a bottom wall (23) and perimeter walls (24) forming an interior cavity for the components. The housing (21) comprises at least one nozzle (25) for air outlet/inlet connection and has an interface panel (26) for user programming. The housing (21) is made with noise insulating walls.

Figure 3:
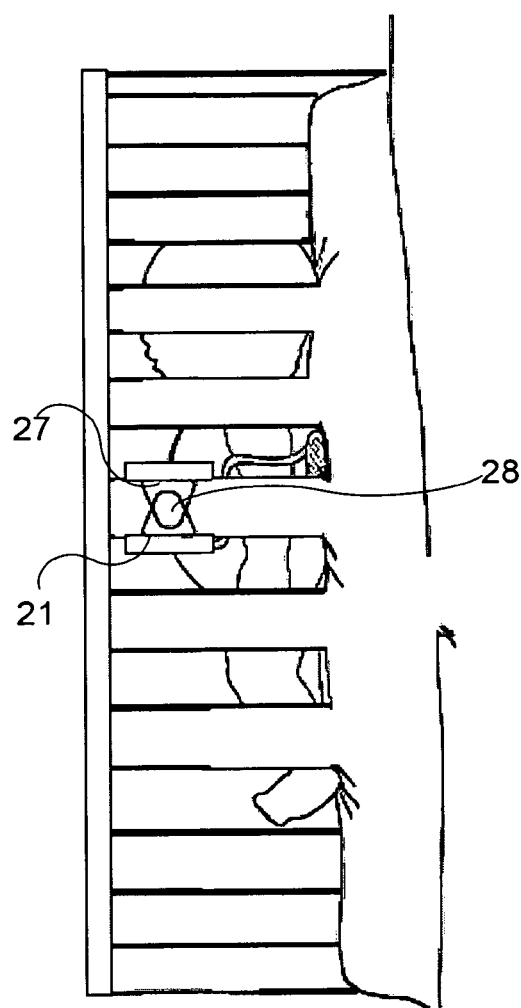
FIG. 3 shows a side view showing the device in use attached to a cradle.

As illustrated in FIG. 3, the housing comprises positioning means in the infant's environment allowing it to be attached to a support or arranged on a surface comprising a flexible band (27) attached to the housing (21) having an adjustable attachment means (28) which is a contact clasp.

Figure 4:
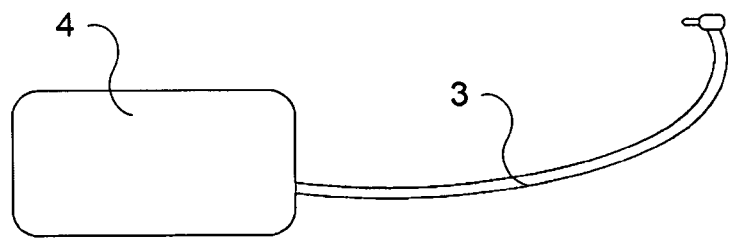
FIG. 4 shows a top view of the inflatable chamber.

Referring to FIG. 4, the simulated breathing pattern transmitting means comprises an inflatable/deflatable chamber (4) that is attached to the infant and a flexible conduit (3) that conveys air from the pump to the chamber.

Figure 5:
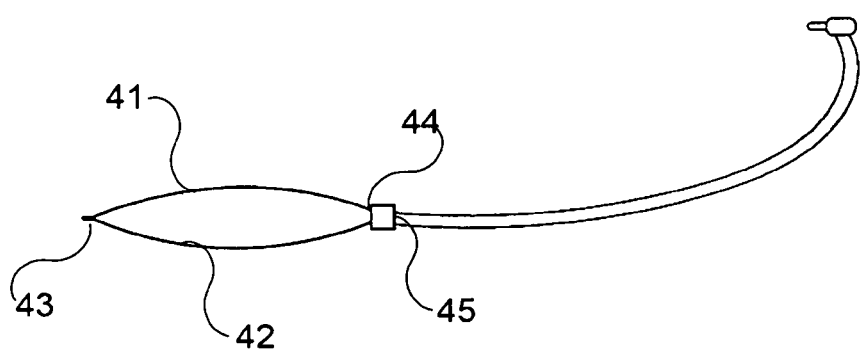
FIG. 5 shows a side view of the inflatable chamber.

As shown in FIG. 5, the chamber (4) is formed by two watertight sheets (41, 42), an upper and a lower one joined at their perimeter edge (43) and retaining a non-joined area (44) where a coupling nozzle (45) is arranged.

Figure 6:
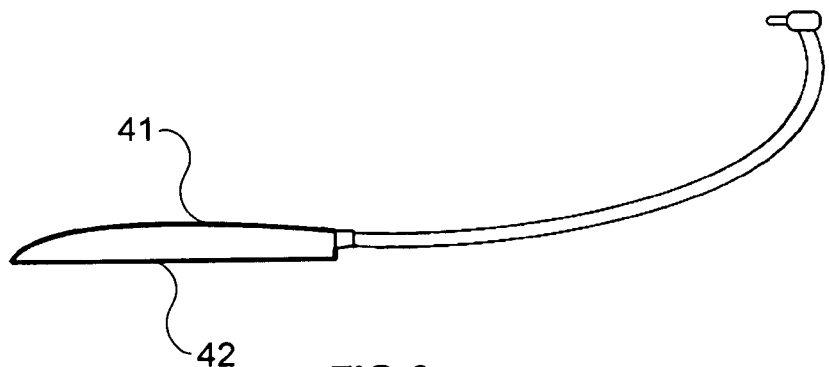
FIG. 6 shows a side view of a second embodiment of the invention.

In an alternative embodiment, schematized in FIG. 6, the upper sheet (41) and the lower sheet (42) are flexible, but in another alternative embodiment the upper sheet (41) is flexible and the lower sheet (42) is rigid.

Figure 7:
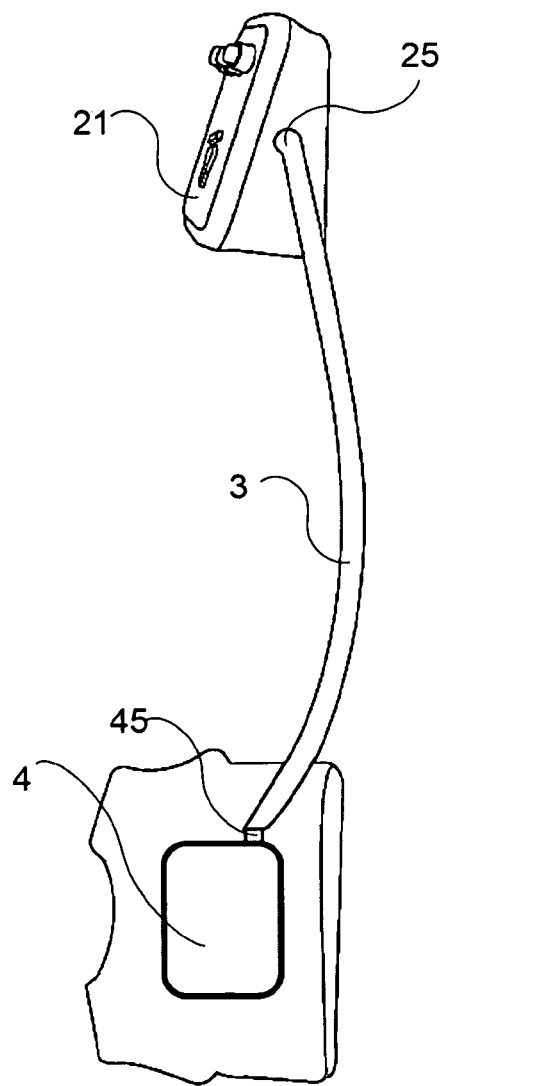
FIG. 7 shows an isometric view of the assembly of the breathing pattern generating means and the piece of garment.

As seen in FIG. 7, the flexible conduit (3) is a hose extending from the connection nipple (25) of the housing (21) to the coupling nipple (45) of the chamber (4).

Figure 8:
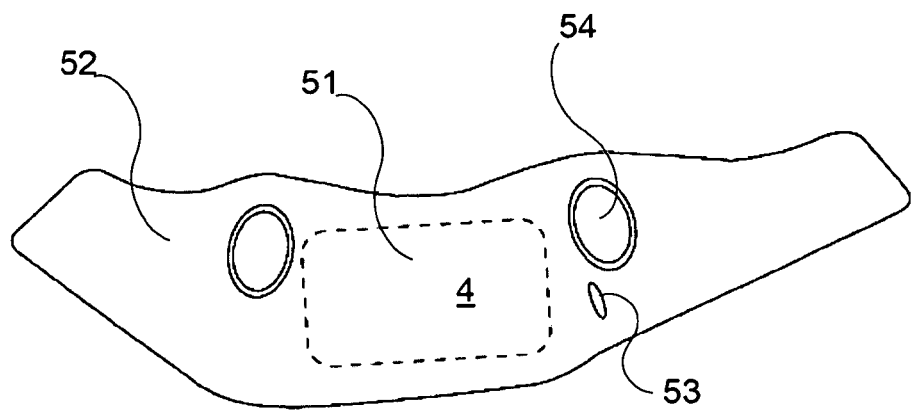
FIG. 8 shows an elevation view of a piece of garment forming part of the device according to one embodiment.

Referring to FIG. 8, the adapting means (5) to the infant's body comprises a pocket-shaped container (51) for housing the chamber (4) which is positioned in a piece of garment (52), wherein the latter has openings (54) for the passage of the user's arms and a side opening (53) for the passage of the flexible hose to the outside of said garment.

Figure 9:
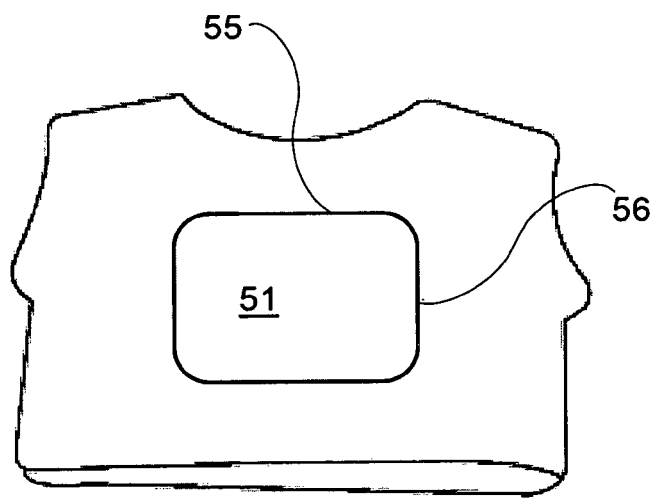
FIG. 9 shows an elevation view of a piece of garment forming part of the device according to a second embodiment.

According to the alternative embodiment shown in FIG. 9, the pocket (51) is formed by at least one upper cover (55) with a side opening (56) for inserting the chamber and allowing the passage of the flexible conduit to the outside. The pocket (51) is attached to the outside of the garment (52), in the back area.

Figure 10:
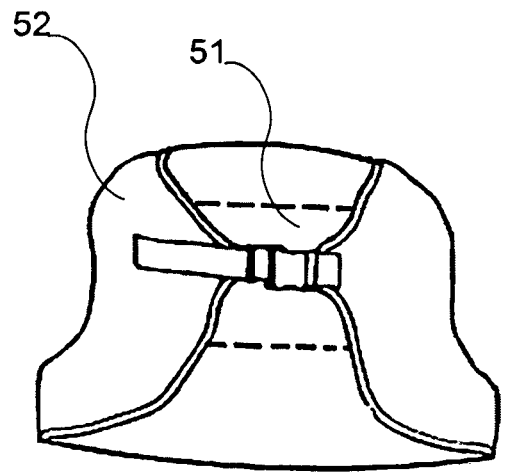
FIG. 10 shows an elevation view of a piece of garment forming part of the device according to a third embodiment.
Figure 11:
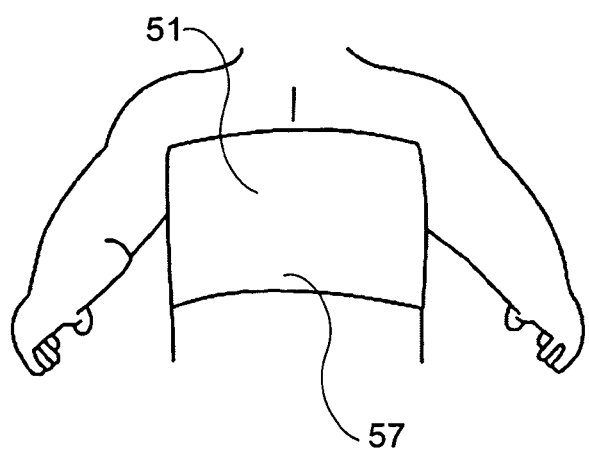
FIG. 11 shows an elevation view of a piece of garment forming part of the device according to a fourth embodiment.

In a preferred embodiment, seen in FIG. 10, the pocket (51) is integrated into a piece of garment (52) wearable on the wearer's torso that closes at the front, the pocket being in the back area, and in an alternative embodiment, best illustrated in FIG. 11, the piece of garment is a girdle (57) adjustable around the perimeter of the torso of the wearer where the pocket (51) is arranged.

Figure 12:
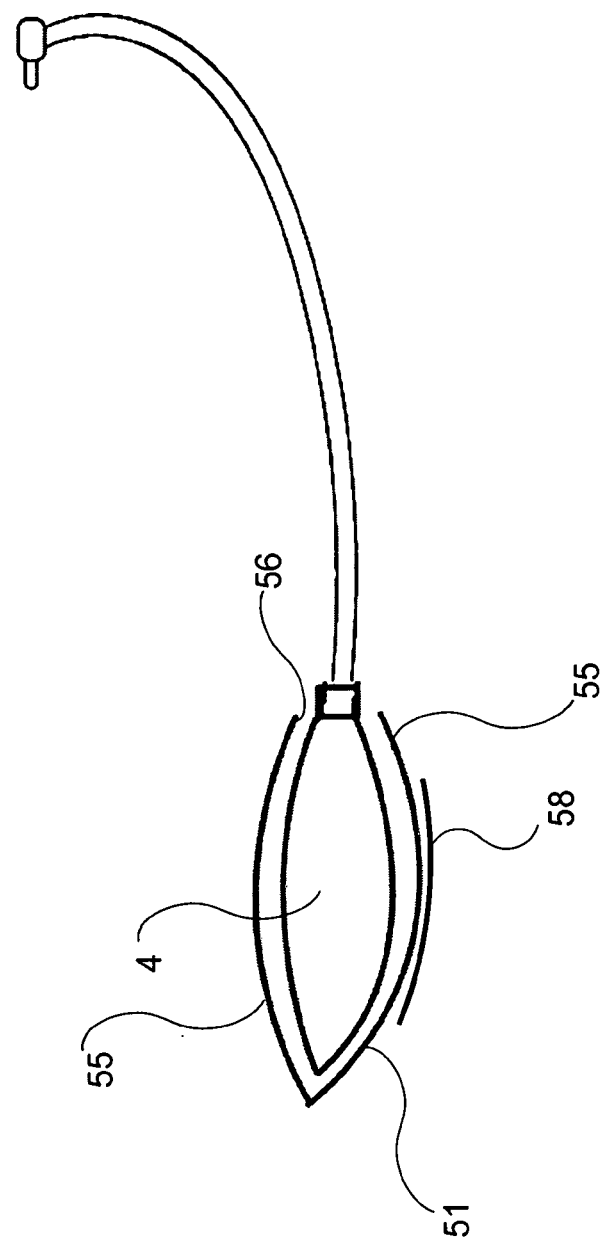
FIG. 12 shows an elevation view of the stimulus transmitting means comprising an inflatable/deflatable chamber and a conduit, according to an alternative embodiment.

In an alternative embodiment schematized in FIG. 12, the pocket (51) may be independent of the piece of garment, and be formed by two flexible and soft covers (55), parallel to each other, and joined incompletely at its perimeter leaving an opening (56) of access to introduce the chamber (4), and comprising removable adhesion means (58) consisting of a contact adhesive patch, located on one of its covers (55) that allow to fix it in a removable manner to a piece of garment (52).

Figure 13:
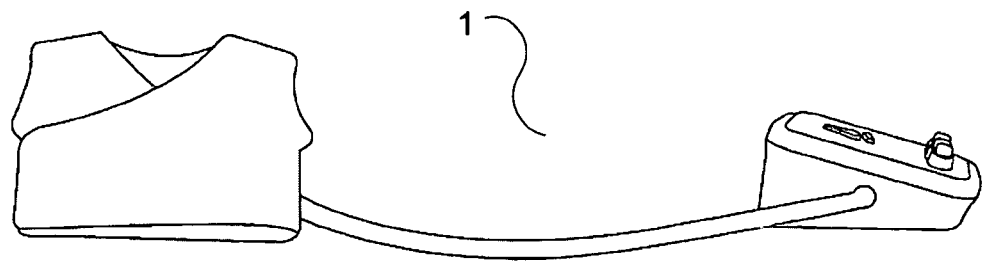
FIG. 13 shows an isometric view of the device according to an individual embodiment.
Figure 14:
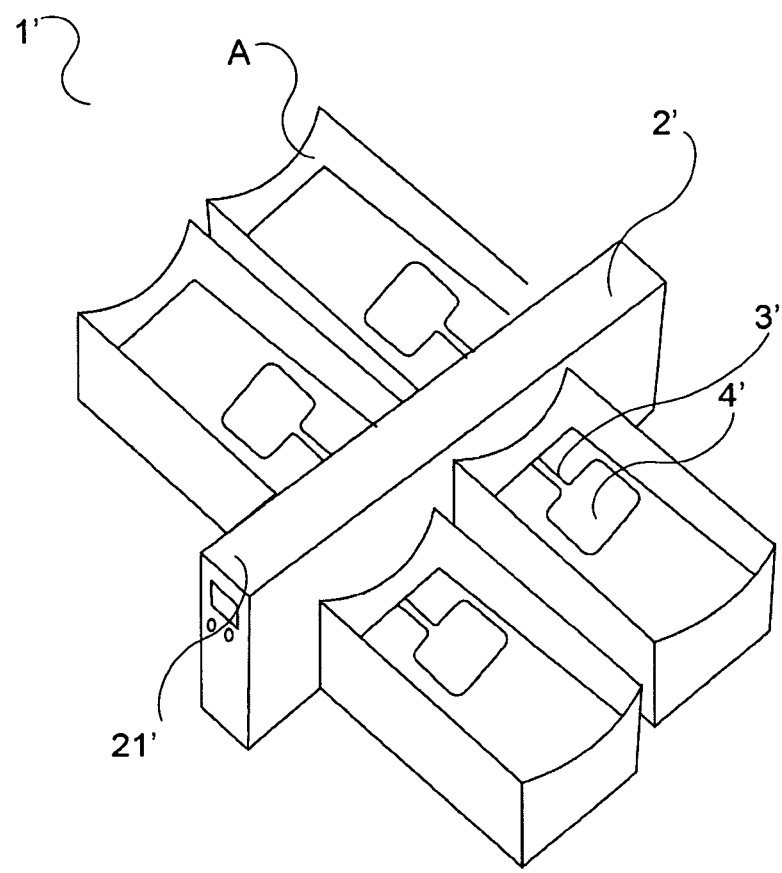
FIG. 14 shows an isometric view of the device according to a multiple modality.
Figure 15:
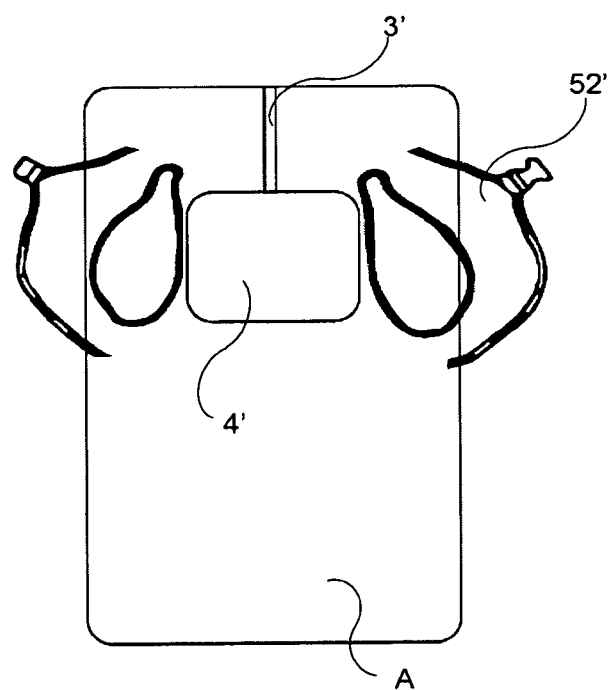
FIG. 15 shows a plan view of a unit forming part of the multiple modality of the device.

In use, as illustrated in FIG. 13, the device (1) can be arranged in a unitary manner for individual use, especially in home use or alternatively, as seen in FIG. 14, the device (1') may be arranged as a whole for hospital use, wherein the breathing pattern generation means (2') has a larger capacity pump, such as to supply three or four devices at a time, which may be arranged in a larger housing (21') in close proximity to units (A) where the infants are located, and providing each unit (A) with the inflation means of a chamber (4') for each unit, wherein each unit also has a piece of garment (52') that receives the chamber (4') which is attached to the pump by its own flexible conduit (3'), as schematized in FIG. 15.

The invention claimed is:

1. A device for preventing apnea episodes in infants that, while being used with a respective infant, simulates a breathing pattern suitable for synchronizing the infant's breathing and that is provided as a tactile direct stimulus arranged in contact with the infant's back while sleeping, comprising:
   a means for generating the breathing pattern, which comprises a means for inflation and a means for deflation, that supply and extract air periodically, emitting air pulses that reach the infant by a means of stimuli transmitter comprising an inflatable/deflatable chamber which is configured to attach to the infant's body;
   an adaptive means that surrounds the infant's torso in a manner as to hold the inflatable/deflatable chamber in contact with the infant's back,
   wherein the means for inflation is an air pump, and the means for deflation is a pneumatic control valve, wherein the means for generating the breathing pattern is user programmable and generates air pulses according to a specific repetitive regime simulating different breathing rates for each respective infant, based on a normal breathing pattern for the respective infant,
   wherein the simulated breathing pattern synchronizes the respective infant's breathing by providing the tactile direct stimulus to the respective infant via the adaptive means, thereby preventing apnea episodes in the respective infant;
   wherein the means for generating the breathing pattern comprises a microcontroller that commands the operation of the means for inflation and the means for deflation to provide the specific repetitive regime simulating different simulated breathing frequencies, and wherein the microcontroller is associated with a safety device with pressure sensors that prevents over-inflation of the chamber or air supply interruption; and
   wherein the means for generating the breathing pattern also comprises a case which houses the means for inflation and the means for deflation, and wherein the case is made of noise insulating walls.

2. The device according to claim 1, wherein the means of inflation is a mechanical or electromagnetic device.

3. The device according to claim 1, wherein the microcontroller is associated with an audible or visual warning device for cases of a malfunction of the device.

4. The device according to claim 1, wherein the means for generating the breathing pattern also comprises a group of backup batteries ensuring the operation of the device in case of interruption of a power supply energizing the device.

5. The device according to claim 1, wherein the case is formed by a rigid body having an upper wall, a lower wall and perimeter walls forming an inner cavity, wherein the case comprises at least one connection nozzle for air outlet/inlet, and the case comprises at least one interface panel for programming by a user.

6. The device according to claim 5, wherein the case comprises means for positioning in the infant's environment allowing the case to be fixed to a support or arranged on a surface.

7. The device according to claim 1, wherein the means for generating the breathing pattern comprises the inflatable/ deflatable chamber that is configured to be attached to the infant and a flexible conduit that conveys air from a pump to the chamber.

8. The device according to claim 7, wherein the inflatable/deflatable chamber is formed by two waterproof sheets, an upper sheet and a lower sheet joined at their perimeter edge which retain an unjoined area where a coupling nozzle is arranged, and wherein the upper sheet is flexible, and the lower sheet is either flexible or rigid.

9. The device according to claim 8, wherein the upper sheet is made of elastomeric material.

10. The device according to claim 8, wherein the flexible conduit is a hose extending from the connection nozzle to the coupling nozzle of the inflatable chamber.

11. The device according to claim 1, wherein the adaptive means to the body comprises a flexible chamber container of the inflatable chamber with means for positioning on an article of clothing and means for arranging a flexible conduit.

12. The device according to claim 11, wherein the flexible chamber container is a pocket formed by at least one top cover with a side opening for passage of the flexible conduit to the outside, and wherein the pocket is integrated in a wearable garment on a torso of the infant.

13. The device according to claim 12, wherein the pocket is attached on the outside or inside of a piece of garment, in a back area of the garment.

14. The device according to claim 11, wherein a piece of garment has openings for the passage of the arms of the infant and a side opening for the passage of the flexible conduit to the outside of said piece of garment.

15. The device according to claim 14, wherein the piece of garment is a girdle adjustable at the perimeter of a torso of the infant.

16. The device according to claim 11, wherein the flexible chamber container is a pocket formed by two parallel, flexible and soft covers, that are incompletely joined at their perimeter leaving an access opening for introducing the inflatable chamber, and comprising removable means for adhesion on one of its covers allowing to fix the flexible chamber to a piece of garment, and wherein the removable means for adhesion of the pocket comprise a contact adhesive patch disposed on the outer surface of one of the covers of the pocket.

17. The device according to claim 1, wherein the device is arranged for hospital use, wherein the means for generating the breathing pattern has a pump of capacity sufficient to supply at least three devices at a time, which may be arranged in a larger case in close proximity to a plurality of units housing a plurality of infants that include the respective infant, and provide each unit with a respective means of inflating a respective chamber for each unit, wherein each unit also has a respective piece of garment that receives the respective chamber which is attached to the pump by a respective flexible conduit.

18. The device according to claim 1, wherein the device is arranged as a single unit for individual at home use.

* * * * *